United States Patent [19]
Decker

[11] 3,982,427
[45] Sept. 28, 1976

[54] APPARATUS FOR WORKING AND TESTING SOLID ELASTOMERS

[76] Inventor: John M. Decker, 6809 Old Chesterbrook Road, McLean, Va. 22201

[22] Filed: June 6, 1975

[21] Appl. No.: 584,377

[52] U.S. Cl. ................................................. 73/101
[51] Int. Cl.² .......................................... G01N 3/32
[58] Field of Search ............... 73/101, 15.6, 100, 91

[56] References Cited
UNITED STATES PATENTS

| | | | |
|---|---|---|---|
| 2,595,069 | 4/1952 | Fritz | 73/100 X |
| 2,735,295 | 2/1956 | Piety | 73/100 |

*Primary Examiner*—Jerry W. Myracle

[57] ABSTRACT

A means and method or process are described in which a sample of solid curable elastomeric material, such as raw or compounded vulcanizable rubber or equivalent, is worked or shear stressed between dies which hold its opposite faces firmly while one of them is gyrated or moved in a small-diameter path about the axis of the other. By this means, a continuous shear stress is applied to the sample over its entire transverse area, there being no relaxing or reversal of the applied forces as in the conventional oscillating systems. The apparatus comprises an upper die, mounted for axial movement towards or away from a lower die whose central vertical axis is slightly offset from the axis of the former. Elastic means bonding the lower die to its mount prevent its rotation but permit flexing and shifting laterally as the lower die is rotated or gyrated in a small circle about the axis of the upper die. This gyration but non-rotation of the lower die stresses the sample uniformly throughout its transverse area, permitting a greater rate of energy input into the sample than earlier systems in which the stress was predominantly in the peripheral area of the sample. Reaction to working in the sample is measured in the form of torque set up in the gyration drive motor; this is sensed and recorded by conventional strain gauge and recording means.

8 Claims, 7 Drawing Figures

APPARATUS FOR WORKING AND TESTING SOLID ELASTOMERS

BACKGROUND AND PRIOR ART

Numerous devices and methods have been proposed and many of them used in the prior art for working and/or testing rubber and other elastomers, e.g., to test rheological, elastic and related properties in test samples of such materials. Standard test procedures have been established by certain agencies, such as the American Society for Testing Materials, the U.S. Bureau of Standards, and various persons and agencies in the rubber and plastic industries. The known procedures are of various types and have been applied in different ways. Among these, the more successful appear to be those in which a sample, e.g., a disc of the material is worked or tested by driving either a rotating or oscillating disc which is embedded in the sample of material. Temperature control means, including heating elements, are incorporated in the dies to (1) permit the measurement of viscosity, and/or (2) promote vulcanization in those materials which cure when subjected to elevated temperatures. In one of the methods proposed to test vulcanizable materials, one of the dies is oscillated angularly with respect to the other about this common axis. This applies a shear stress or a working to the material; in the usual case, the internal resistance of the sample to such working increases towards a desired or predetermined maximum and the torque applied to oscillate the die, which reflects the degree of curing, etc., is measured by suitable sensing devices to provide a record of the procedure and its effect on the sample. Some devices are useful only for testing viscosity in solid and semi-solid elastomers, etc. Some of the latter are driven in continuous rotation. These may be very satisfactory for determining viscosity of raw or compounded rubbers at low temperatures but are not desirable for testing vulcanizable materials at curing temperatures because the sample materials would be rapidly destroyed in the test procedure.

Hence, in testing vulcanizable elastomers, it has been usual practice to grip the sample between opposed axially aligned dies and then to oscillate one of the dies or a biconical disc embedded in the sample, through a small angle or rotation about the common die axis, applying a shear stress first in one direction and then in the other, successive applications of the stress passing through zero. In general, the prior art discloses a non-rotatable die, usually the upper, which can be raised or lowered to release or grip the sample against a lower die which, in some cases, is mounted to be oscillated by a motor driven lever or rocker arm. Heating means, such as electrical resistance elements, are usually incorporated in the dies for heating the sample to curing temperature and for controlling the temperature throughout the test.

The devices just mentioned all have one important deficiency. The degree or amplitude of shear applied is a maximum at the periphery of the sample and zero at its center; hence, the sample is worked unevenly. There is a tendency to tear the sample loose from the dies at its outer edges, whereas the central part is hardly worked at all. Also, in the case of the oscillating disc cure meter the disc not only acts as a heat sink and retards the cure, but the twist in the disc shaft and yielding of the torque arm results in a strain loss of up to 50 percent with some rubbers. A primary object of the present invention is to overcome these deficiencies, using an apparatus and method which in some respects is quite similar to those of prior art but in other respects is very different.

Some workers in the prior art have recognized the deficiencies mentioned above but they have not succeeded in eliminating them. It has been proposed, for example, to reduce the angle of oscillation to reduce the strain loss and slippage at the periphery of the sample. While this is partially effective for the purpose stated, it reduces even further the degree of working accomplished at and near the center of the sample. Thereby it limits the maximum torque (resistance to working) in the sample and renders the curemeter or testing device less sensitive to minor changes in the elastomer than it would be if a larger angle of oscillation, and consequently a larger energy input, could be tolerated. See the 1974 book of ASTM standards, Method D2084, for example.

The deficiencies mentioned above, and others inherent in the prior art systems contribute to difficulties in obtaining good graphical records or representations, as pointed out, for example, in the patent to Wise, U.S. Pat. No. 3,387,490, mentioned above. For this reason, Wise has proposed a complication in recording that would desirably be avoided. See also, an article by Decker et al. in *Rubber World*, December, 1962, where recording problems are discussed further. Briefly stated, when the stress applied is rapidly reversed, passing through zero repeatedly, as noted above, peaks or spikes are shown which confuse rather than elucidate the results being achieved. The true state of curing, for example, must be indicated in such cases by a true envelope of the oscillating peaks, and must be interpolated manually or mentally or else a complicated recording system must be resorted to. In contrast, according to the present invention, a smooth, definitive curve, properly indicative of actual results, is readily obtained.

The present invention is based to a large degree on the discovery by the present inventor that the above deficiencies can be largely or entirely eliminated by changing the sample working or shear-stressing operation to a simple, continuous, non-reversing gyratory action. In this system, one die, e.g., the lower, is mounted for relatively free rotation, with respect to its driver, on a continuously driven rotary driver whose axis is eccentric to, i.e. offset a small distance from the axis of the upper die. With the sample gripped by its more or less plane faces between the relatively fixed die and the gyrating die, the latter is resiliently restrained from actual rotation while being carried in a small-diameter circle around the axis of the upper die; the lower face of the sample is stressed in shear continuously and all of its area, transversely, is subjected to the same amplitude of distortion or stress. More energy can be put into the working without damaging any part of the sample due to overworking, and the sensitivity of the test is greatly improved. The tests can be carried out more rapidly and/or curing is faster than with the oscillating disc curemeter because the elimination of the conventional disc greatly improves heat transfer.

DESCRIPTION OF PREFERRED EMBODIMENT

Figure 1:
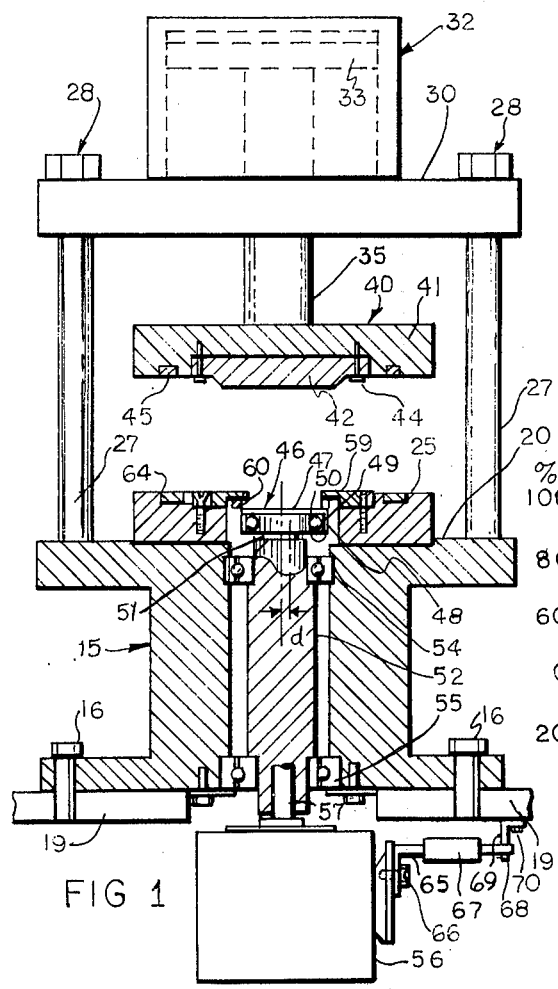
FIG. 1 is a vertical sectional view through a preferred apparatus embodiment of the invention.
Figure 1A:
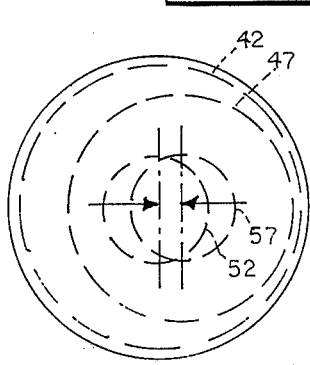
FIG. 1A is a diagrammatic view illustrative of the relative gyratory motion of the opposed dies.

In FIG. 1 there is shown in vertical section a preferred apparatus for practicing the present invention. This is an instrument designed as a convenient tool for curing elastomers. such as vulcanizable rubber and analogous materials, and for determining important rheological and other properties of the material, such as its viscosity scorch time, curing rate, time to optimum cure, flow characteristics, and other properties commonly of interest in such materials.

The apparatus of this invention comprises a main frame member 15 having plane or substantially plane upper and lower flanges and a hollow cylindrical body connecting them together in a single rigid structure. It is secured by suitable fastening means, such as bolts 16, to a support table or other surface or frame member or members 19. The main frame member 15 has an upper substantially flat and horizontal table surface 20, suitably formed to support and hold in place a lower die confining ring or annular block member 25. The latter is fixed to table surface 20 by any suitable means, such as by welding or by use of bolts, not shown. Extending upwardly from table surface 20 are upright posts 27, of which two are shown. A greater number may be used if needed or desired. Posts 27 extend through openings in an upper horizontal plate 30, to which they are securely fastened by nuts 28. Plate 30 supports a hydraulic cylinder 32 which may be supplied with operating hydraulic fluid from any suitable source, not shown, for driving a piston 33 up or down, as needed. A downwardly extending piston rod or shaft 35 extends from the piston to support solidly and rigidly a base plate 41 of an upper die shown generally at 40. The actual die member 42 is secured to base 41 by means of screws 44 or equivalent. The lower face of die 42 is formed with a grid or cross-hatching of fine cut lines 43. The spacing, width, and depth of these lines may be varied as needed; in a typical case, spacing of about 1 mm., with a depth of about 0.2 mm., was found to be very satisfactory. See FIG. 1B. The grid of grooves 43 is designed to hold firmly to the upper face of an elastomer sample S, shown in enlarged scale in FIG. 2, which also shows the dies 40 and 46 in cooperating or closed relationship.

The upper base plate 41 is provided with a heating element 45 seated in a groove in its lower face and annularly spaced from the die 42 proper, as is conventional in devices of this general character. Electric power is supplied to the heating element, which usually is of the resistance type, by means not shown but obvious.

Figure 1B:
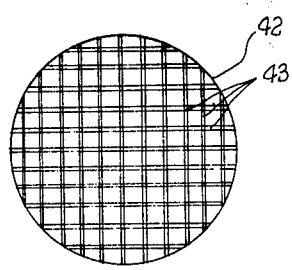
FIG. 1B is a face view of the upper die, or of either die, showing a preferred form of sample-gripping surface.

The lower die is shown generally at 46. It comprises the die 47 proper, in the form of a disc with a downturned peripheral flange 48 which is formed to receive and hold an electrical resistance heating element 49 for temperature control. The upper surface of die 47 is preferably cross gridded or grooved in the same manner as shown in FIG. 1B. The die 47 proper is mounted on the outer race of a ball bearing 50, or equivalent anti-friction bearing, supported on the slightly eccentrically displaced upper neck or extension 51 of a vertical drive shaft 52. Shaft 52 is shown substantially in axial alignment with shaft 35. The arrangement is such that the die 47, although free to rotate with respect to neck 51, does not rotate per se but gyrates around the axis of shaft 35 as well as 52 when shaft 52 is driven in rotation, due to the eccentric offset of the neck 51. Shaft 52 is mounted in bearings 54 and 55 within the hollow cylindrical body of main frame member 15. It is adapted to be driven in continuous rotation by a drive motor 56 which is attached to shaft 52 through a drive connector 57 at the lower end of the shaft.

Figure 2:
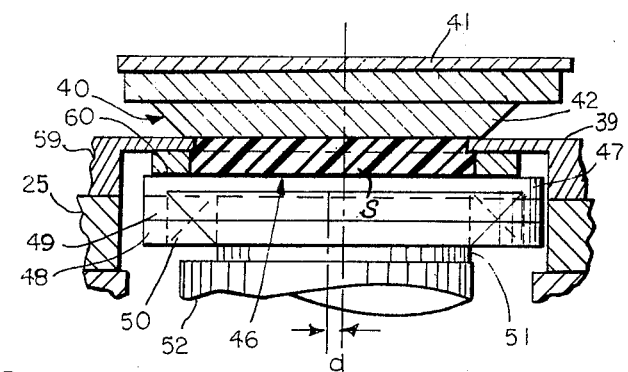
FIG. 2 is an enlarged fragmentary view of the dies, partly in section, showing them in changed positions relatively, as compared with FIG. 1.

The lower die 47 per se is held against rotation, yieldingly but effectively, by means of a seal ring or bond member 60 formed of high temperature heat-resistant rubber such as a silicone rubber; a suitable material is available commercially under the trade name "Silastic 745U". Other and equivalent material can be used, so long as it allows the die disc 47 to gyrate with respect to the upper die while restraining it from rotation. FIG. 2 is an enlarged fragmentary view, showing in more detail than FIG. 1 the relationship between the dies, their axes, and associated parts. The actual displacement of the axis of the lower die with respect to the upper is quite small dimensionally, of the order of 0.5 mm., in a typical case. It is shown somewhat exaggerated in FIG. 2, the displacement being indicated at $d$.

The gyrating controlling ring or bond 60 is securely fastened to the die 47 and to the surrounding structure, ring 25, through an overlying ring 59. Preferably, the bonding ring is vulcanized to both die 47 and ring 59. As the die gyrates, the rubber bond ring 59 yields enough to allow this gyration without damage to the bond member, its material and cross section being chosen to permit such operation. At the same time, of course, the die 47 is not permitted to rotate per se. Ring 25 is cut out in the center to provide an opening sufficiently larger than the diameter of the die 47 to permit gyratory motion of the latter. This ring is provided also with a heating element at 63, seated in an annular groove 64 which surrounds but is spaced outwardly from the ring 59 that holds the die 47 against rotation.

To hold drive motor 56 from rotating under the reaction torque at the dies, an arm 65 is secured to it by a bolt or screw 66. This arm is connected into a stress transducer 67 of known type, which comprises strain gauge elements for measuring and recording the reaction torque. This torque of course results from the reaction against shear in the sample being worked. It causes a slight bending of shaft or arm 65 which is detected by a strain gauge load cell in the unit 67. The torque values thus sensed are communicated in conventional manner to recording equipment. That is, an electrical signal from the sensitive strain gauge cell is fed to an appropriate data presentation device of a type that is well known and constitutes no part of the present invention. Arm stop means 69 is secured to frame member 19 by a bolt 70.

Referring to FIG. 2, which shows the dies and associated parts in larger scale than in FIG. 1, it will be understood that the piston in FIG. 1 within cylinder 32 has been driven down hydraulically to engage upper die 42 firmly against the upper part of face of a sample S that is to be tested. This sample is of generally disc or wafer shape, but it does not necessarily have plane upper and lower faces, but may be somewhat convex. For convenience, it may be said that the upper and lower faces of the sample, which are to be engaged by the respective die surfaces 42 and 47, are perpendicular to the axes of the sample and of the dies, it being understood that the sample faces need not be plane or flat. While the grooved or knurled under surface of upper die 42 engages the top face of sample S, the top face of die 47 similarly engages its lower face and both dies engage so effectively that there is no slippage when the lower die is gyrated by rotation of shaft 52 which carries die 47 in a small circular path of gyration of radius $d$. This causes some flexing of bond ring 60 which yields, however, to permit the gyratory action required, as explained above.

Figure 3:
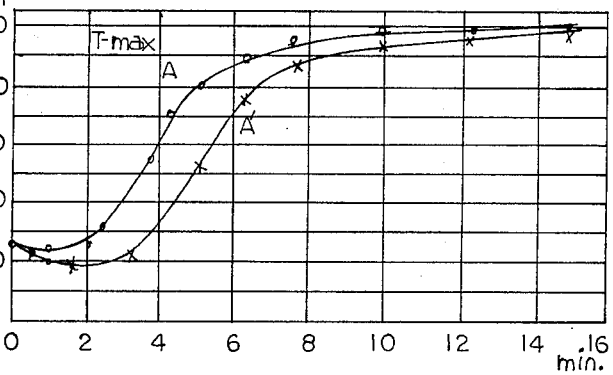
FIG. 3 is a graph showing typical test results of use of the present method as compared with prior art oscillating disk method on a typical elastomer sample.

The internal resistance of the elastomer sample S to the applied shear forces normally increases, slowly at first, then more rapidly, and finally more slowly again. At last a maximum value of torque, $T_{max}$, is reached, which is typical of the full torque of resistance of the particular elastomer being tested. Assume, for example, that for a typical elastomer of particular composition, the maximum torque to be expected is about 50 inch-pounds. As the composition is being worked in the test apparatus, the torque increases from a fairly low value to higher and higher values, as the time of working increases. FIG. 3 shows graphically the results of testing certain samples by the apparatus and method of the present invention compared with test results by a typical prior art oscillating disk apparatus of the type referred to above. The curves A and A' show results on a sample of tire tread stock. In the upper curve A, the sample showed a torque of 97 percent of $T_{max}$ after 8 minutes of curing whereas the older test apparatus, curve A', required about 14 minutes of curing to reach the same level.

As indicated above, the prior art apparatus does not transfer heat from the dies to the specimen as rapidly as does the present invention. Curing time, therefore, is substantially reduced.

Figure 4:
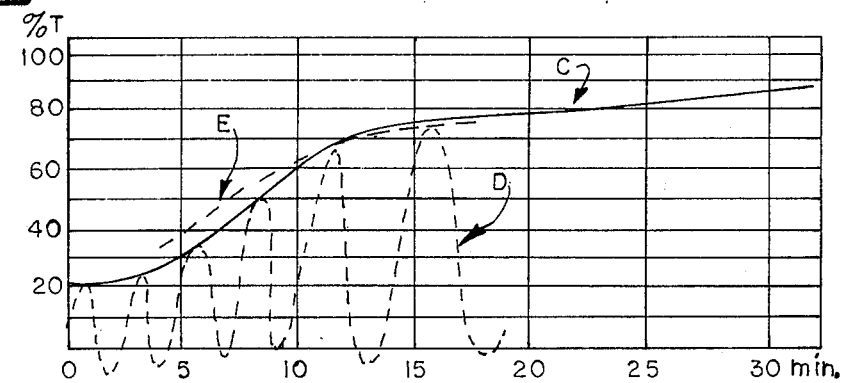
FIG. 4 is another graphical view, showing a typical record obtainable in the apparatus and procedure of the present invention as compared with prior art.

FIG. 4 shows a typical recorder diagram, in curve C, from the present invention, compared with the widely oscillating curve of the prior art systems, shown at D. With the curve D, an envelope shown dotted at E, must be derived for the record to have full meaning. The smooth curve C is much simpler, more accurate, and more convenient.

Figure 5:
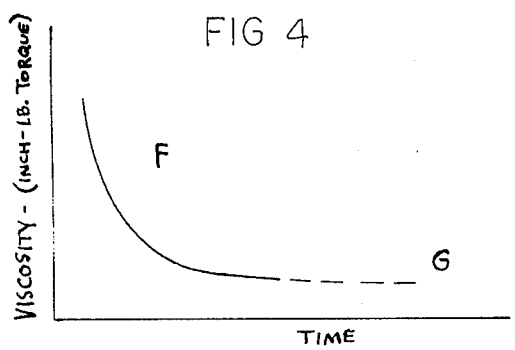
FIG. 5 is a graph showing typical results using the present method to measure viscosity.

FIG. 5 shows a typical curve F obtained by using the apparatus of this invention to determine viscosity. In such cases, working lowers the viscosity (the material does not cure) to an ultimate minimum level G.

In summary, the present invention in its method aspects. involves the application of shear stressing or working the sample by engaging opposed faces thereof by respectively immobile and gyrating dies so that displacement of the elastomer sample in shear, i.e., the displacement of the lower face with respect to the upper in FIGS. 1 and 2, is applied at once to the whole area, transversely speaking, of the sample. All parts of the lower face, for example, are displaced to a similar distance, with respect to corresponding points on the upper surface. In general terms, the opposed faces are engaged by holding members (dies) whose central axes are substantially perpendicular to the sample faces (and to the die faces) and are parallel but do not coincide. The offset is small but highly important; in a typical case it may be of the order of 0.5 mm. In other cases it may be more or less.

Apparatus-wise, the invention comprises a combination of opposed dies which face each other and have parallel but non-coinciding axes substantially perpendicular to their faces (the faces may not be flat in many cases) and means are provided for gyrating one die by moving it around the axis of the other in a small circle while resiliently holding the gyrating die against rotation per se (by means of bond ring 60).

It will be self-evident that variations and modifications may be made in method and particularly in apparatus without departing from the spirit and purpose of the invention. For example, the upper die may be gyrated and the lower held still, or the same die that is gyrated may also be mobile, or mounted to be moved into and out of engagement with the sample to be tested. Other arrangements will suggest themselves to those skilled in the art.

It is intended by the claims which follow to cover the invention and its obvious equivalents and variations as broadly as the state of the prior art properly allows.

What is claimed is:

1. Apparatus for shear stressing a sample of solid elastomer which sample has opposed faces lying generally in parallel planes substantially perpendicular to a central axis of the sample, said apparatus comprising, in combination, a frame, a first sample-engaging die mounted in said frame for holding one face of said sample having an axis adapted to be set parallel to said sample central axis, a second die also mounted to said frame for engaging the other face of said sample and having an axis also adapted to be set parallel to the central axis of the sample, said second die axis being aligned parallel with but not coincident with the axis of the first die, and drive means for gyrating the second die without rotation of said second die per se in a path of small radius around the axis of said first die.

2. Apparatus according to claim 1 which comprises a rotatable drive shaft mounted with its axis substantially in alignment with the axis of said first die, an eccentric on said drive shaft for supporting said second die with its axis not coincident with the axis of the first die, and elastic means for restraining the first die against rotation when said shaft is rotated to gyrate said second die.

3. Apparatus according to claim 1 which comprises a fixed ring surrounding said second die and an elastic bonding member securing said second die to said ring.

4. Apparatus according to claim 1 which comprises a shaft for gyrating said second die, a motor for driving said shaft in rotation, and means for measuring the reaction torque exerted by the sample in resisting the shear stressing resulting from the gyration movement of said second die.

5. Apparatus according to claim 4 in which the reaction torque measuring means comprises an arm attached to the drive motor, and arm stopping means on the frame, said torque measuring means being responsive to a bending moment of force applied to said arm.

6. Apparatus according to claim 1 in which the first die is mounted for translational movement towards and away from said sample.

7. Apparatus according to claim 1 in which the dies are grooved transversely in a grid pattern to enhance their hold on the sample faces.

8. Apparatus according to claim 1 in which the drive means for gyrating the second die comprises a drive shaft mounted in bearings in said frame with its axis substantially in alignment with the axis of the first die, an eccentric extension on said shaft with its axis substantially in alignment with the axis of the second die, a drive motor engaged in driving relationship with said shaft, and a torque measuring means attached to said motor and comprising strain guage means for measuring and recording the torque exerted by said motor in shear stressing the sample.

* * * * *